United States Patent [19]

Neufeld

[11] Patent Number: Plant 7,335

[45] Date of Patent: Sep. 25, 1990

[54] PLUM TREE, "FIRST BEAUT"

[76] Inventor: Charles H. Neufeld, 38250 Road 52, Kingsburg, Calif. 93631

[21] Appl. No.: 405,771

[22] Filed: Sep. 11, 1989

[51] Int. Cl.[5] ..... A01H 5/00

[52] U.S. Cl. ..... Plt./38

[58] Field of Search ..... Plt./38

[56] References Cited

U.S. PATENT DOCUMENTS

| | | | |
|---|---|---|---|
| P.P. 2,539 | 6/1965 | Anderson | Plt. 38 |
| P.P. 4,394 | 3/1979 | Zaiger | Plt. 38 |
| P.P. 4,621 | 1/1981 | Kitahara et al. | Plt. 38 |

*Primary Examiner*—James R. Feyrer

*Attorney, Agent, or Firm*—Godfrey & Kahn

[57] ABSTRACT

A new and distinct variety of plum tree denominated varietally as First Beaut which is somewhat similar to the Red Beaut plum tree (U.S. Plant Pat. No. 2,539) with which it is most closely related, but which is distinguished therefrom and characterized principally as the novelty by producing fruit which are mature for commercial harvesting and shipment approximately May 15 through May 20 in the San Joaquin Valley of Central California, the subject variety maturing for commercial harvesting and shipment approximately five days earlier than the Red Beaut plum tree at the same geographical location.

1 Drawing Sheet

BACKGROUND OF THE NEW VARIETY

The present invention relates to a new and distinct variety of plum tree, hereinafter denominated varietally as "First Beaut" and more particularly to a plum tree which is broadly similar to the "Red Beaut" plum tree, U.S. Plant Pat. No. 2,539, with respect to most of its physical characteristics, but which is distinguished therefrom, and characterized principally as to novelty by producing fruit which are ripe for commercial harvesting and shipment approximately five days in advance of the Red Beaut plum tree, under the ecological conditions prevailing in Tulare County, Calif. in the central portion of the San Joaquin Valley. Further, the subject variety produces a semi-clingstone fruit which has a pleasing shape and an attractive skin color.

ORIGIN AND ASEXUAL REPRODUCTION OF THE NEW VARIETY

The inventor has spent a substantial portion of his professional life engaged in farming operations. In this regard, the applicant, during routine orchard operations on May 15, 1986, discovered a mutation of a Red Beaut plum tree (U.S. Plant Pat. No. 2,539) growing within the cultivated area of his commerical orchard which is located south of the corner of Avenue 384 and Road 32 in Tulare County, Calif. The fruit produced by the mutation were noted at that time to have desirable characteristics and the inventor subsequently marked the mutation for future observation.

To determine whether the traits of the newly discovered variety of plum tree were true, the inventor, during the winter of 1986, removed bud wood from the aforementioned mutation and grafted it into test trees which were growing on the same orchard property. The inventor has continuously observed these test trees for the past two years and has evaluated the fruit produced therefrom, and it has subsequently been determined that the progeny produced from these test trees have the same identical characteristics as that produced by the original mutation.

The "First Beaut" plum tree hereof is characterized principally as to novelty by bearing semi-clingstone fruit which have an attractive red skin color and which further are ripe for commercial harvesting and shipment approximately five days earlier than the Red Beaut plum tree (U.S. Plant Pat. No. 2,539) under the ecological conditions prevailing in the San Joaquin Valley of Central California. The new variety of plum tree matures, and is ripe for commercial harvesting and shipment approximately 15 May through 20 May in the San Joaquin Valley of Central California.

BRIEF DESCRIPTION OF THE DRAWINGS

The accompanying drawing is a color photograph of four mature fruit of the subject variety, one of which has been divided in the axial plane to show the flesh characteristics, together with a twig bearing representative leaves which display the coloration of the top and bottom surfaces thereof, and a representative stone, all of the subject variety.

DETAILED DESCRIPTION

Referring more specifically to the pomological details of this new and distinct variety of plum tree, the following has been observed under the ecological conditions prevailing at the applicant's orchard which is located south of the corner of Avenue 384 and Road 32 in Tulare County, Calif. All major color code designations are by reference to the Dictionary of Color by Maerz and Paul, Second Edition, 1950, or alternatively, by reference to the Inter-Society Color Council—National Bureau of Standards. Common color names are also employed occasionally.

TREE

Generally:

*Size.*—Generally — above average.

*Vigor.*—Above average.

*Form.*—Generally — upright and broadly spreading at commercial maturity. The final form and density of the subject plum cultivar is determined by pruning practices.

*Productivity.*—Productive, when adequately pollinated. The variety is considered hardy when grown under typical San Joaquin Valley climatic and ecological conditions.

Trunk:

*Diameter.*—Generally considered large in diameter as compared with other common plum varieties.

*Texture.*—Moderately rough. A moderate amount of scarf skin is readily apparent.

*Bark color.*—Gray to grayish-brown, (7-C-7 through 7-E-8).

*Lenticels.*—Number — an average number of lenticels are present.

Branches:

*Size.*—Average, occasionally above average in thickness.

*Bark color.*—Mature branches have a dark gray to grayish-brown color, (7-C-8 through 8-H-8).

*Immature shoots.*—Color — generally a bright green color is evident, (18-J-6). Further, some exposed areas of immature shoots may be tinged with the color red. However, this color is not distinctive of the subject variety. New terminal growth on expanding shoots are strongly tinged with red.

LEAVES

Size:

*Generally.*—Medium to large as compared with other plum tree varieties.

*Average length.*—Approximately 11.2 cm. This dimension includes the petiole.

*Average width.*—Approximately 4.8 cm.

Leaf form:

*Generally.*—Obovate.

Apex:

*Form.*—Acute and slightly twisted.

Color:

*Upper surface.*—Medium green, (b 22-L-8); (125. m. Ol G).

*Lower surface.*—A pale green, (21-J-6); (120. m. Y G).

Leaf margin:

*Form.*—Generally considered coarsely crenate; generally doubly so at mid-margin.

Petiole:

*Average length.*—Approximately 9 through 13 mm.

*Average thickness.*—Approximately 2 mm.

*Color.*—Pale green, although occasionally tinged with red, (20-K-4);(121 p.Y G).

Leaf glands:

*Size.*—Small.

*Form.*—Globose.

*Numbers.*—Variable, however, most commonly two large glands are positioned at the base of the leaf margin, and two somewhat smaller glands are positioned on the leaf blade just above the base of the leaf margin.

*Color.*—On immature growth, the leaf glands color appears yellow-green, (20-K-6). The leaf glands, however, turn to a chestnut-red color, (7-L-9) and thereafter deteriorate with advancing senescence.

Stipules:

*Size.*—Generally considered small and early deciduous.

*Average length.*—Approximately 5 through 6 mm.

*Form.*—Narrowly lanceolate and having a serrate margin.

*Color.*—Immature stipules displays a pale green color, (20-J-4). The color of the stipules darken and deteriorate with advancing senescence.

FLOWERS

Date of bloom: Early as compared with the bloom dates of other common plum cultivars growing in the San Joaquin Valley of Central California. During the 1988–1989 season, full bloom was observed on Mar. 1, 1989 in the orchard of origin which is located in Tulare County, Calif.

Size:

*Generally.*—Average; occasionally slightly above average.

*Diameter.*—Approximately 13 through 16 mm when fully expanded. It was noted that the flowers of the subject variety have a tendency to remain slightly cupped, inwardly, even at full maturity.

Bloom quantity:

*Generally.*—Abundant.

Bud scales:

*Color.*—The bud scales have a dark chestnut-brown color, (8-L-11).

Flower buds:

*Size.*—Medium.

*Form.*—Conic.

*Numbers.*—Generally two floral buds appear in each node.

Petals:

*Size.*—Medium.

*Average length.*—Approximately 8 through 9 mm.

*Average width.*—Approximately 7 through 8 mm.

*Form.*—Ovate.

*Color.*—White, (1-A-1).

Petal claw:

*Length.*—Short and having a moderate amount of venation over the surface thereof.

Petal margin:

*Form.*—Appearing quite undulate; this characteristic is quite evident in the vicinity of the petal apex.

Petal apex:

*Form.*—The apex is cupped inwardly quite substantially.

Pedicel:

*Length.*—Variable, approximately 6 through 8 mm.

*Thickness.*—Approximately 0.75 through 1 mm.

*Color.*—A light yellow-green, (17-J-5).

Nectaries:

*Color.*—Tan-green, (12-L-3). This color darkens with advancing senescence.

Anthers:

*Size.*—Average.

*Color.*—Generally a pale pink, (1-D-1). This color may appear slightly darker along the anther margin.

Pollen:

*Generally.13* Lacking. The variety appears substantially pollen sterile.

Stamen:

*Average length.*—Approximately 5 through 7 mm. The length of the stamen appears slightly shorter than the pistil.

*Color.*—White, (1-A-1).

Pistil:

*Average length.*—Approximately 9 through 10 mm.

*Color.*—A pale yellow-green, (17-K-5).

*Surface texture.*—Glabrous.

FRUIT

Maturity when described: Ripe for commercial harvesting and shipment approximately 15 May through 20 May under the ecological conditions prevailing in Tulare County, in the central portion of the San Joaquin Valley of Central California.

Size:

*Generally.*—Medium as compared with the fruit produced by other plum cultivars and uniform. The size of the subject fruit is considered good for the early date of maturity.

*Average diameter in the cheek plane.*—Approximately 47 mm.

*Average diameter in the suture plane.*—Approximately 46 mm.

*Average diameter in the axial plane.*—Approximately 44 mm.

Uniformity: Slightly variable but generally considered ovate in its lateral aspect. The variety is nearly globose in its apical aspect, and further appears slightly asymmetrical with one fruit side slightly larger than the other.

Suture:

*Generally.*—The suture appears as a thin shallow line which extends from the base to apex and further blends in well with respect to color with the surrounding skin. As a general matter, the suture deepens somewhat within the basal stem cavity.

Ventral surface:

*Shape.*—Rounded, and slightly lipped.

Stem cavity:

*Shape.*—Small, narrow and moderately deep.

*Form.*—Oval.

*Average depth.*—Approximately 9 through 10 mm.

*Average width.*—Approximately 15 through 20 mm.

*Average length.*—Approximately 20 through 22 mm.

Base:

*Shape.*—Generally considered rounded and occasionally appearing slightly truncate. The base angle is generally at right angles to the fruit axis.

Apex:

*Form.*—Somewhat variable but it generally appears rounded and may occasionally appear slightly raised.

Pistil point:

*Position.*—The pistil point appears slightly oblique. The pistil point is small but distinct.

Stem:

*Length.*—Generally considered average in length, its length being approximately 11 through 13 mm.

*Thickness.*—Approximately 2 mm.

*Color.*—Light green, (20-K-5).

Skin:

*Average thickness.*—Medium.

*Surface texture.*—Average, glabrous.

*Tenacious to flesh.*—Yes.

*Tendency to crack.*—Not observed.

*Acidity.*—Low.

*Color.*—Generally the fruit of the subject variety has a substantially uniform red-purple skin color, (6-L-6), (40. S. r Br).

Ground color: At commercial maturity, no ground color is usually visible.

Bloom:

*Generally.*—At commercial maturity, the fruit surface is uniformly covered with a light-gray bloom. Further, a small amount of light-colored flecking and dots are apparent around the apex and apical shoulders.

Flesh color:

*Generally.*—The flesh color has a light amber-yellow color (10-I-6); (86. l. Y). The flesh color may appear slightly darker in the area just directly under the skin, (71. m. OY).

Pit cavity:

*Color.*—A dark amber-brown, (12-F-8), (69. deep OY).

Fibers:

*Color.*—Numerous light colored fibers of moderate length but having fine textures are found in the flesh.

Flesh texture:

*Generally.*—Firm, fine textured and juicy, especially with advancing maturity.

Ripening:

*Generally.*—Even.

Flavor: Generally considered mild, pleasant, and low acid.

Aroma: Slight.

Eating quality: The variety is considered good for such an early date of maturity.

STONE

Attachment:

*Generally.*—The subject variety is considered to be a semi-clingstone fruit. Flesh fibers will cling laterally over the stone surfaces.

Size:

*Generally.*—Small.

*Average length.*—Approximately 17.8 mm.

*Average width.*—Approximately 16.3 mm.

*Average thickness.*—Approximately 8.5 mm.

Fibers:

*Generally.*—Numerous short fibers are evident. These fibers are attached primarily to lateral stone surfaces.

Form: Irregular, appearing at times oval and occasionally ovate.

Base:

*Shape.*—Broad and rounded on the ventral suture side, and rounded and occasionally truncate on the dorsal suture side. Base angle is variable but generally appears slightly oblique with respect to the stone axis. Further, the base is shorter on the ventral suture side.

Hilum:

*Size.*—Small, narrow and substantially eroded.

Apex:

*Shape.*—Rounded and having a short, sharp tip.

Sides:

*Size.*—Appearing slightly unequal.

Surface texture: Moderately smooth with a netted pattern which has very low ridges over the lateral surfaces. A series of grooves are evident over the basal shoulder area, the grooves converge basally.

Ventral edge:

*Generally.*—A prominent narrow wing is present and extends from the base to the apex, the ventral edge being more prominent in the area from mid-suture to the hilum. A moderately wide and deep groove, which at times is discontinuous, is present, and is located in a position roughly parallel to the ventral edge at a location approximately 3 through 4 mm below the edge. This deep groove converges apically and basally. It has been determined that other smaller grooves may be present in the same general area, but these are usually not as prominent. The basal portion, of approximately 4 through 5 mm, of the ventral edge is substantially eroded.

Dorsal edge:

*Generally.*—A characteristically wide groove is evident along the dorsal edge from the base of the stone to a location somewhat well above mid-stone. Two ridges subtend by the groove and appear rather jagged or scalloped. The dorsal suture narrows to a thin edge from a location just above mid-stone to the apex.

Color: The stone color, when dry, is a light tan, (11-H-4).

Tendency to split: Not observed.

Fruit use: The new variety "First Beaut" produces a fresh market plum for both local markets and for long distance shipping.

Although the new variety of plum tree possesses the described characteristics as a result of the growing conditions prevailing in the San Joaquin Valley of Central California, it is to be understood that variations of the usual magnitude and characteristics incident to growing conditions, fertilization, pruning and pest control are to be expected.

Having thus described and illustrated my new variety of plum tree, what I claim is:

1. A new and distinct variety of plum tree to be denominated varietally as First Beaut substantially as illustrated and described and which is characterized principally as to novelty by its production of fruit which are somewhat similar in their overall appearance and other physical characteristics to the fruit produced by the Red Beaut plum tree (U.S. Plant Pat. No. 2,539) from which it was derived as a chance mutation, but which is distinguished therefrom by producing fruit which are ripe for commercial harvesting and shipment approximately five days earlier than the fruit produced by the Red Beaut plum tree.

* * * * *

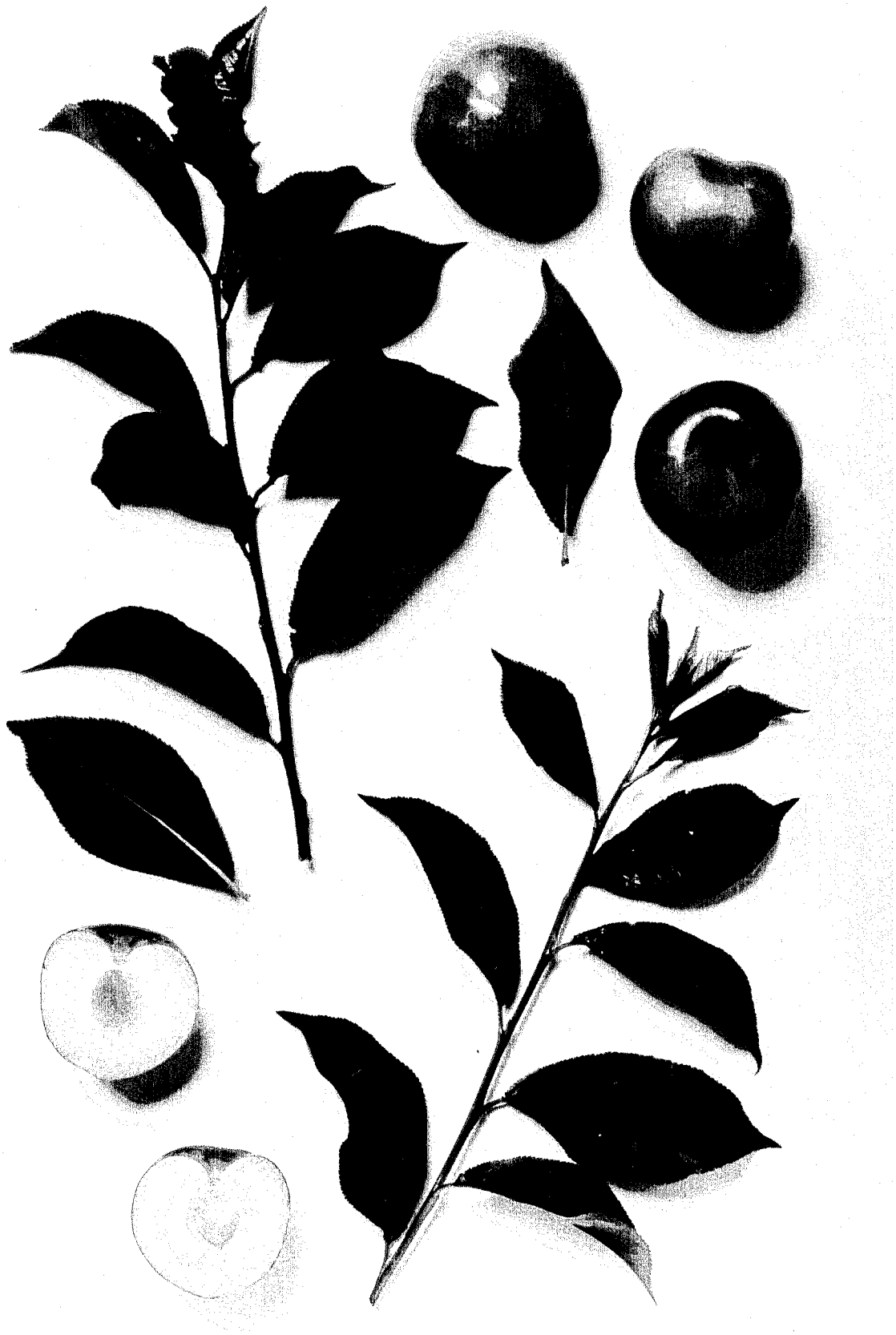

UNITED STATES PATENT AND TRADEMARK OFFICE

CERTIFICATE OF CORRECTION

PATENT NO. : Plant 7, 335

DATED : September 25, 1990

INVENTOR(S) : CHARLES H. NEUFELD

It is certified that error appears in the above-identified patent and that said Letters Patent is hereby corrected as shown below:

Column 3, Line 38, cancel "(b 22-L-8);" and insert
--- (22-L-8); ---;

Column 4, Line 59, after "Generally." cancel "13".

Signed and Sealed this

Tenth Day of December, 1991

*Attest:*

HARRY F. MANBECK, JR.

*Attesting Officer*

*Commissioner of Patents and Trademarks*